United States Patent
Tanackovic Abbas-Terki et al.

(10) Patent No.: US 11,535,894 B2
(45) Date of Patent: *Dec. 27, 2022

(54) METHOD AND KIT FOR PREDICTING THE RISK OF DEEP VEIN THROMBOSIS AND PULMONARY EMBOLISM

(71) Applicant: GENE GENDER S.R.L., Milan (IT)

(72) Inventors: Goranka Tanackovic Abbas-Terki, Lausanne (CH); Joëlle Michaud Schutz, Lausanne (CH); Thierry Daniel Pache, Lausanne (CH)

(73) Assignee: GENE GENDER S.R.L., Milan (IT)

( * ) Notice: Subject to any disclaimer, the term of this patent is extended or adjusted under 35 U.S.C. 154(b) by 263 days.

This patent is subject to a terminal disclaimer.

(21) Appl. No.: 16/468,183

(22) PCT Filed: Dec. 11, 2017

(86) PCT No.: PCT/EP2017/082157
§ 371 (c)(1),
(2) Date: Jun. 10, 2019

(87) PCT Pub. No.: WO2018/104545
PCT Pub. Date: Jun. 14, 2018

(65) Prior Publication Data
US 2020/0032339 A1 Jan. 30, 2020

(30) Foreign Application Priority Data

Dec. 9, 2016 (EP) .................................. 16203285
Mar. 30, 2017 (EP) .................................. 17163894

(51) Int. Cl.
*C12Q 1/68* (2018.01)
*C12Q 1/6883* (2018.01)
*G16B 20/20* (2019.01)

(52) U.S. Cl.
CPC .......... *C12Q 1/6883* (2013.01); *G16B 20/20* (2019.02); *C12Q 2600/106* (2013.01); *C12Q 2600/118* (2013.01); *C12Q 2600/156* (2013.01)

(58) Field of Classification Search
None
See application file for complete search history.

(56) References Cited

U.S. PATENT DOCUMENTS

| 2009/0270332 A1* | 10/2009 | Bare ...................... G01N 35/00 514/56 |
| 2010/0227776 A1* | 9/2010 | Wu ...................... C12Q 1/6886 506/13 |
| 2014/0045177 A1 | 2/2014 | Jiang et al. |
| 2015/0272935 A1 | 10/2015 | Walker, Jr. et al. |

FOREIGN PATENT DOCUMENTS

EP 2535424 A1 * 12/2012 .......... C12Q 1/6827

OTHER PUBLICATIONS

Illumina "GoldenGate Genotyping A New Evolution in High Throughput Screening," Aug. 18, 2009, available via URL: <. illumina.com/documents/seminars/presentations/2009_08_downing_jason.pdf> (Year: 2009).*
[Illumina "GoldenGate Genotyping A New Evolution in High Throughput Screening," Aug. 18, 2009, available via URL: <. illumina.com/documents/seminars/presentations/2009_08_downing_jason.pdf>, retrieved on Dec. 8, 2021 retrieved from internet. (Year: 2009).*
Bruzelius et al. Predicting venous thrombosis in women using a combination of genetic markers and clinical risk factors. Journal of Thrombosis and Haemostasis; 2014; 13: 219-227. (Year: 2014).*
Lin et al. Association of genetic loci for migraine susceptibility in the she people of China. The Journal of Headache and Pain; 2015; 16; 70: 1-7. (Year: 2015).*
Winsvold et al.Genetic analysis fora shared biological basis between migraine and coronary artery disease. Neurol Genet 2015; 1: e10: p. 1-12. (Year: 2015).*
Blanco-Molina et al. Progestin-only contraception and venous thromboembolism. Thrombosis Research; 2012; 129; 5: e257-e262. (Year: 2012).*
Dahm et al. Candidate gene polymorphisms and the risk for pregnancyrelated venous thrombosis. British Journal of Haematology; 2012; 157: 753-761. (Year: 2012).*
Blaisdell. Acquired and Congenital Clotting Syndromes. World J. Surg.; 1990; 14: 664-669. (Year: 1990).*
Previtali et al. Risk factors for venous and arterial thrombosis. Blood Transfus; 2011; 9:120-138. (Year: 2011).*
Hinds et al. Genome-wide association analysis of self-reported events in 6135 individuals and 252 827 controls identifies 8 loci associated with thrombosis. Human Molecular Genetics; 2016; vol. 25; No. 9: 1867-1874. (Year: 2016).*
Susan (CMAJ; 2011; 183(18): p. E1278-E1279). (Year: 2011).*
Wang et al. Hum Genet; 2012; 131:1337-1344. (Year: 2012).*
Bruzelius et al. Journal of Thrombosis and Haemostasis; 2014; 13: 219-227. (Year: 2014).*
Blanco-Molina et al. Thrombosis Research; 2012; 129; 5: e257-e262. (Year: 2012).*
Dahm et al. British Journal of Haematology; 2012; 157: 753-761. (Year: 2012).*

(Continued)

*Primary Examiner* — Jeanine A Goldberg
*Assistant Examiner* — Wahwah T Johnson
(74) *Attorney, Agent, or Firm* — Oliff PLC

(57) ABSTRACT

Specific single nucleotide polymorphisms (SNPs) in the human genome, and their association with deep vein thrombosis (DVT) and related pathologies, such as pulmonary embolism (PE).

6 Claims, No Drawings
Specification includes a Sequence Listing.

(56) References Cited

OTHER PUBLICATIONS

Lin et al. The Journal of Headache and Pain; 2015; 16; 70: 1-7. (Year: 2015).*
Morange et al., "Genetics of Venous Thrombosis: update in 2015," Thrombosis and Haemostasis, 2015, vol. 114, No. 5, pp. 910-919.
De Haan et al., "Multiple SNP testing improves risk prediction of first venous thrombosis," Blood, Jul. 19, 2012, vol. 120, No. 3, pp. 656-663.
Mar. 23, 2018 International Search Report issued in International Patent Application No. PCT/EP2017/082157.

* cited by examiner

SEQUENCE LISTING

<160> NUMBER OF SEQ ID NOS: 11

<210> SEQ ID NO 1
<211> LENGTH: 51
<212> TYPE: DNA
<213> ORGANISM: Homo sapiens
<220> FEATURE:
<221> NAME/KEY: misc_feature
<222> LOCATION: (26)..(26)
<223> OTHER INFORMATION: n is c or t

<400> SEQUENCE: 1
gatggggaag aggagcattg aggacngtgt tcaagaggaa gcccgctgcc t        51

<210> SEQ ID NO 2
<211> LENGTH: 51
<212> TYPE: DNA
<213> ORGANISM: Homo sapiens
<220> FEATURE:
<221> NAME/KEY: misc_feature
<222> LOCATION: (26)..(26)
<223> OTHER INFORMATION: n is c or t

<400> SEQUENCE: 2
tggatggtat tgacttttac atcacngaag gtgtttccat agatggaaga c        51

<210> SEQ ID NO 3
<211> LENGTH: 51
<212> TYPE: DNA

```
<213> ORGANISM: Homo sapiens
<220> FEATURE:
<221> NAME/KEY: misc_feature
<222> LOCATION: (26)..(26)
<223> OTHER INFORMATION: n is a or g

<400> SEQUENCE: 3
tgtaagagca gatccctgga caggcnagga atacaggtat tttgtccttg a          51

<210> SEQ ID NO 4
<211> LENGTH: 51
<212> TYPE: DNA
<213> ORGANISM: Homo sapiens
<220> FEATURE:
<221> NAME/KEY: misc_feature
<222> LOCATION: (26)..(26)
<223> OTHER INFORMATION: n is a or g

<400> SEQUENCE: 4
gttcccaata aaagtgactc tcagynagcc tcaatgctcc cagtgctatt c          51

<210> SEQ ID NO 5
<211> LENGTH: 51
<212> TYPE: DNA
<213> ORGANISM: Homo sapiens
<220> FEATURE:
<221> NAME/KEY: misc_feature
<222> LOCATION: (26)..(26)
<223> OTHER INFORMATION: n is - or g

<400> SEQUENCE: 5
gcagtaggaa ggatgtcctc gtggtnaccc cttggctggc tcccattgtc t          51

<210> SEQ ID NO 6
<211> LENGTH: 51
<212> TYPE: DNA
<213> ORGANISM: Homo sapiens
<220> FEATURE:
<221> NAME/KEY: misc_feature
<222> LOCATION: (26)..(26)
<223> OTHER INFORMATION: n is - or c

<400> SEQUENCE: 6
ccaagaacca ccaggcggtc cggaanccgt gagcggctgc caggggctct g          51

<210> SEQ ID NO 7
<211> LENGTH: 51
<212> TYPE: DNA
<213> ORGANISM: Homo sapiens
<220> FEATURE:
<221> NAME/KEY: misc_feature
<222> LOCATION: (26)..(26)
<223> OTHER INFORMATION: n is c or g

<400> SEQUENCE: 7
gcgatgttaa ttactctcca gccccntcag aaggggctgg attgatggag g          51

<210> SEQ ID NO 8
<211> LENGTH: 51
<212> TYPE: DNA
<213> ORGANISM: Homo sapiens
<220> FEATURE:
<221> NAME/KEY: misc_feature
<222> LOCATION: (26)..(26)
<223> OTHER INFORMATION: n is c or t

<400> SEQUENCE: 8
gtgagggtga ggcttgtctc tctctngccc tctcatcctg gcacatgtgc g          51
```

```
<210> SEQ ID NO 9
<211> LENGTH: 51
<212> TYPE: DNA
<213> ORGANISM: Homo sapiens
<220> FEATURE:
<221> NAME/KEY: misc_feature
<222> LOCATION: (26)..(26)
<223> OTHER INFORMATION: n is a or g

<400> SEQUENCE: 9
agggatccaa tcgtcatcac tctgtntggg agctggtgat ataggaggca t          51

<210> SEQ ID NO 10
<211> LENGTH: 21
<212> TYPE: DNA
<213> ORGANISM: Artificial Sequence
<220> FEATURE:
<223> OTHER INFORMATION: forward primer

<400> SEQUENCE: 10
gccaccgtgt ccactactat g                                           21

<210> SEQ ID NO 11
<211> LENGTH: 20
<212> TYPE: DNA
<213> ORGANISM: Artificial Sequence
<220> FEATURE:
<223> OTHER INFORMATION: reverse primer

<400> SEQUENCE: 11
gtccacgcac accaggtaat                                             20
```

METHOD AND KIT FOR PREDICTING THE RISK OF DEEP VEIN THROMBOSIS AND PULMONARY EMBOLISM

The present application contains a Sequence Listing that has been submitted electronically in ASCII format and is hereby incorporated by reference in its entirety. The ASCII copy, created on May 31, 2022, is named Substitute_Sequence_Listing_ST25.txt and is 2,762 bytes in size.

TECHNICAL FIELD

The invention relates to the field of medicine, in particular to the field of blood clotting diseases prognosis. Specifically, the present invention relates to specific single nucleotide polymorphisms (SNPs) in the human genome, and their association with deep-vein thrombosis (DVT) and related pathologies, such as pulmonary embolism (PE).

BACKGROUND OF THE INVENTION

Venous thrombosis is a serious medical condition that occurs when a blood clot (thrombus) forms in one or more veins of the body. One particular form of venous thrombosis is called deep vein thrombosis (DVT) when the blood clot occurs in deep veins. Such blood clots might travel through the bloodstream and lodge in lungs, where they can block blood flow, causing pulmonary embolism (PE).

Venous thrombosis is a complex multifactorial disease, several inherited or acquired conditions can increase coagulability of blood and thus the tendency to develop blood clots. The inherited conditions include mutations in the diverse well-known clotting anticoagulant or thrombolytic factors genes, such as the factor V Leiden gene, and the prothrombin factor II gene. Additional mutations can be present in genes coding for proteins C and S, although they increase risk of developing venous thrombosis significantly, they are rare and most of them are practically private. Other likely inherited causes include a possible increase in the expression of procoagulant factors such as factor VIII, von Willebrand factor, and factors IX and XI (Cushman M., (2005), Hematology Am Soc Hematol Educ Program: 452-457). In addition, non-O ABO blood groups, with exception of the A2 group, were demonstrated as increasing the risk of developing thrombosis, as well as some additional genetic variants in the genes such as FGG, GP6, KNG1, PROCR, SLC44A2, STXBP5 and TSPAN15 were associated to an increased risk of venous thrombosis (Morange P-E., Suchon P. and Trégouët D-A., (2015), Thrombosis and Haemostasis 114 (5): 910-919). The examples of the acquired conditions that can cause DVT are surgery and trauma, prolonged immobilization, cancer, myeloproliferative disorders, and even pregnancy and post-partum (Seligsohn U. and Lubetsky A., (2001) New Eng J Med 344(16): 1222-1231). Thus, DVT might occur as the result of a genetic mutation alone or in concert with behavioral and environmental factors, such as prolonged immobilization, smoking and hormonal treatments (e.g. use of hormonal contraceptives or hormone replacement therapy for menopause).

Venous thrombosis occurs in 1-2 per 1,000 individuals per year. The incidence increases with age, from 1 in 100,000 in children to 1 in 10,000 individuals in the reproductive age and 1 in 1,000 individuals at the age 50 to 60 (Rosendaal F. R., (2016), Thromb J 14(Suppl 1): 117-121). As mentioned, numerous hereditary and acquired conditions were demonstrated in relation with an increased risk of developing DVT, nonetheless widely-accepted evidence of haemostatic abnormalities associated with thrombophilia includes the following parameters: antithrombin deficiency, protein S deficiency, protein C deficiency, factor V Leiden mutation, prothrombin G20210A mutation, non-O ABO blood groups, high levels of factor VIII dysfibrinogenaemia and hyperhomocysteinaemia (Franchini M., Martinelli I. and Mannucci P. M., (2016), Thrombosis and Haemostasis 115: 25-30). These parameters are also included in the standard thrombophilia testing, which thus includes only few genetic markers (the factor V Leiden mutation, the prothrombin G20210A mutation and eventually non-O blood groups).

Over 100 million women worldwide use combined estroprogestative contraceptives (CC), due to their very high effectiveness in reducing the risk of unwanted pregnancy and their beneficial effect on diverse symptoms related to women's cycle. Nonetheless, these contraceptives also increase the risk of blood clotting substantially, which can ultimately lead to DVT and PE (Vinogradova Y., Coupland C. and Hippisley-Cox J., (2015) BMJ 350: h2135). Newer generations of the CC, the so-called 3rd and 4th generations CC, are usually better tolerated by women but importantly, they increase the risk of developing DVT even more than the older preparations of the so-called $2^{nd}$ and $1^{st}$ generations.

The incidence of thrombosis among CC users is around 1‰ or 10 times more than in population in general at the same age. In France alone, where over 3 M women aged 15-49 use CC, the National Agency for the Safety of Drugs and Health Products reports every year over 2,500 cases of DVT, 850 cases of PE, and 20 cases of death linked to contraceptive pills. According to recent estimates, in Europe, 22,000 DVT cases related to CC occur each year. Thus, one of the major challenges for healthcare professionals is to identify women at risk of developing blood clotting disease related to CC such as DVT and PE, and advise them on alternative contraception methods.

As the standard of care nowadays, prescribing physicians use a medical questionnaire to assess the risk of thrombosis, mostly focusing on age, body mass index and smoking habits that are known risk factors for disease development, as well as on the personal and familial history of DVT or related diseases. If the familial or personal history of thrombosis is positive, physicians might use the first-level laboratory test for thrombophilia screening that includes analysis of only 2 genetic risk factors: the factor V-Leiden and the prothrombin mutation; eventually, some laboratories, also include genetic tests allowing to assess for the ABO blood groups. Though these genetic factors are well-established risk factors for thrombosis development, they explain less then one third of the inherited risk to develop thrombosis. Preciseley, factor V-Leiden is present among 20% of patients that develop thrombosis, whereas only 6% of patients carry the prothrombin mutation (Rosendaal F. R. and Reitsma P. H., (2009); Journal of Thrombosis and Haemostasis 7(1): 301-304). Presence of the non-O ABO blood group, with exception of the A2 blood group, increases the risk of developing thrombosis but it was demonstrated as a particularly important risk factor when combined with factor V-Leiden mutation due to additive effect (Franchini M. and Mannucci P. M., (2014), Thrombosis and Haemostasis 112 (6): 1103-1109).

Taking into account the currently registered number of thrombosis cases related to CC, as well as the small proportion of thrombosis patients that are carriers of the genetic variants included into the standard testing, this approach is a relatively low performing one, with suboptimal sensitivity and specificity. This observation is further confirmed through diverse studies that demonstrate that these informations, notably familial history, are insufficient to reliably estimate risk of DVT (de Haan H. G. et al., (2012), Blood 120: 656-663; Suchon P, et al., (2015), Thrombosis and Haemostasis 114(6)).

For women in the period of menopause, hormone replacement therapy (HRT) aims to prevent discomfort caused by diminished circulating estrogen and progesterone hormones in woman's body, or in the case of the surgically or prematurely menopaused women, it aims at prolonging life and reducing the occurrence of osteoporosis and dementia. It involves use of preparations that usually include estrogens and progesterone or progestins. As in the case of contraceptive treatments, these hormones and consequently the replacement treatments increase importantly the risk of developing DVT and PE. It is now well established that the presence of the factor V Leiden mutation and prothrombin mutation has a multiplicative effect on the overal risk of DVT related to homone replacement therapy (Douketis J. D. et al., (2011), Clin Appl Thromb Hemost. 17(6): E106-113; Botto N., et al., (2011), Climacteric. 14(1): 25-30).

Methods of genetic epidemiology estimate that heritability of DVT is around 50% (Morange P-E., Suchon P. and Trégouët D-A., (2015), Thrombosis and Haemostasis 114 (5): 910-919). Thus, considering the incidence of DVT and PE in human beings, there is a strong need to identify new genetic factors involved in the risk of developing blood clotting diseases.

SUMMARY OF THE INVENTION

The present invention provides a prognostic method for identifying if a subject is at risk of developing a blood clotting disease, the method comprising determining in a sample from said subject the genotype of at least one single nucleotide polymorphism selected from the group consisting of rs1799853 (SEQ ID NO: 1) and rs4379368 (SEQ ID NO: 2).

The invention also provides a kit for use in said prognostic method, comprising
i) Detection reagents for detecting single nucleotide polymorphisms selected from the group consisting of rs1799853 (SEQ ID NO: 1) and rs4379368 (SEQ ID NO: 2); and optionally
ii) Instructions for use.

The invention further provides a computer program or a computer-readable media containing means for carrying out for identifying if a subject is at risk of developing a blood clotting disease, the method comprising determining in a sample from said subject the genotype of at least one single nucleotide polymorphism selected from the group consisting of rs1799853 (SEQ ID NO: 1) and rs4379368 (SEQ ID NO: 2).

DETAILED DESCRIPTION OF THE INVENTION

The present invention relates to the identification of novel single nucleotide polymorphisms (SNPs) and unique combinations of such SNPs in a subject or patient, as well as combination of SNPs and clinical risk factors that are associated with a risk of developing blood-clotting diseases.

In particular, the present invention provides a prognostic method for identifying if a subject is at risk of developing a blood clotting disease, the method comprising determining in a sample from said subject the genotype of at least one single nucleotide polymorphism (SNP) selected from the group consisting of rs1799853 (SEQ ID NO: 1) and rs4379368 (SEQ ID NO: 2).

As used in the specification and claims, the singular forms "a", "an" and "the" include plural references unless the context clearly dictates otherwise.

The term "comprise" is generally used in the sense of include, that is to say permitting the presence of one or more features or components.

As used herein the term "subject" or "patient" is used interchangeably herein to refer to both young and old human beings of both sexes. The term does not denote a particular age. For example, the subject is healthy or a subject is in need of a treatment or with a disease or disorder. Preferably, the subject is a human undergoing a change in hormone levels. More preferably, said subject is a woman undergoing a change in hormone levels. In another embodiment, the subject is a woman undergoing a change in particular female hormone levels, either induced by any treatment that involves hormone and/or by any particular naturally occurring change in a woman's life that modifies hormone levels. In particular, treatments include contraceptives, combined contraceptives, progestin-only contraceptives, hormone replacement therapy, assisted reproductive technology, and naturally occurring changes in a woman's life such as for example pregnancy and postpartum periods.

"Combined contraceptive" refers to any contraceptives that contain an estrogen combined with a progestin.

As used herein, the term "blood clotting disease" refers to diseases selected from the group comprising vein thrombosis, deep vein thrombosis (DVT), pulmonary embolism (PE) and arterial thrombosis.

As used herein, the term "at risk" when used with respect to developing a blood clotting disease refers to a subject which is more predisposed and likely to develop a blood clotting disease than a non "at risk" subject.

The present invention also provides a prognostic method for identifying if a subject undergoing a change in hormone levels is at risk of developing a blood clotting disease, the method comprising determining in a sample from said subject the genotype of rs1799853 (SEQ ID NO: 1) or rs4379368 (SEQ ID NO: 2).

Preferably, the present invention provides a prognostic method for identifying if a subject undergoing a change in hormone levels is at risk of developing a blood clotting disease, the method comprising determining in a sample from said subject the genotype of rs1799853 (SEQ ID NO: 1) and rs4379368 (SEQ ID NO: 2).

The invention also relates to a prognostic method for identifying if a subject is at risk of developing a blood clotting disease, the method comprising determining in a sample from said subject the genotype of at least one single nucleotide polymorphism (SNP) selected from the group consisting of rs1799853 (SEQ ID NO: 1) and/or rs4379368 (SEQ ID NO: 2), wherein said method further comprises determining the genotype of at least one single nucleotide polymorphism (SNP) selected from the group consisting of rs6025 (SEQ ID NO: 3), rs1799963 (SEQ ID NO: 4), rs8176719 (SEQ ID NO: 5), rs8176750 (SEQ ID NO: 6), rs9574 (SEQ ID NO: 7), rs2289252 (SEQ ID NO: 8), and rs710446 (SEQ ID NO: 9).

The invention further relates to a prognostic method for identifying if a subject is at risk of developing a blood clotting disease, the method comprising determining in a sample from said subject the genotype of at least one single nucleotide polymorphism (SNP) selected from the group consisting of rs1799853 (SEQ ID NO: 1) and/or rs4379368

(SEQ ID NO: 2), wherein said method further comprises determining the genotype of single nucleotide polymorphisms (SNP) selected from the group consisting of rs6025 (SEQ ID NO: 3), rs1799963 (SEQ ID NO: 4), rs8176719 (SEQ ID NO: 5), rs8176750 (SEQ ID NO: 6), rs9574 (SEQ ID NO: 7), rs2289252 (SEQ ID NO: 8), and rs710446 (SEQ ID NO: 9).

In a particular embodiment, the subject is a woman subject undergoing a change in hormone levels.

Thus, according to one embodiment, the invention relates to a prognostic method for identifying if a woman subject undergoing a change in hormone levels is at risk of developing a blood clotting disease, the method comprising determining in a sample from said woman subject the genotype of at least one single nucleotide polymorphism (SNP) selected from the group consisting of rs1799853 (SEQ ID NO: 1) and rs4379368 (SEQ ID NO: 2).

The present invention also provides a prognostic method for identifying if a woman subject undergoing a change in hormone levels is at risk of developing a blood clotting disease, the method comprising determining in a sample from said woman subject the genotype of rs1799853 (SEQ ID NO: 1) or rs4379368 (SEQ ID NO: 2).

As used herein, the "p-value" determines the statistical significance of the prognostic method of the invention comprising determining in a sample from said subject the genotype of rs1799853 (SEQ ID NO: 1) and/or rs4379368 (SEQ ID NO: 2). A small p-value (typically <0.05) indicates strong evidence of the association of rs1799853 and rs4379368 with blood clotting diseases such as DVT and/or PE.

As shown in example 1, the determination of the genotype of rs1799853 and rs4379368 provides statistically significant evidence of the association with blood clotting diseases, in particular DVT and/or PE with a p-value of $5 \cdot 10^{-4}$ and $3.6 \cdot 10^{-2}$ respectively (Example 1, Table 6).

A Receiver Operating Characteristic (ROC) curve is established and measures how well the different models discriminate the subject at risk from the subject without risk. The true positive rate (TPR) is plotted against the false positive rate (FPR) at various threshold settings (Fawcett T., (2006), *Pattern Recognition Letters.*, 27: 861-874). The accuracy is measured by the area under the ROC curve ("AUC").

As used herein, the "AUC" (Area Under the Curve) defines the probability that a positive test ranks higher than a negative test in order to discriminate between the subject at risk and without risk. The AUC ranges from 0.5 (50%—no predictive value) to 1 (100%—perfect discrimination; Fawcett T., (2006), *Pattern Recognition Letters.*, 27: 861-874).

As shown in example 1, the determination of the genotype of rs1799853 (SEQ ID NO: 1) and/or rs4379368 (SEQ ID NO: 2) improves the performance of the prognostic method for determining women at risk of developing a blood clotting disease compared to the standard genetic testing of rs6025 (SEQ ID NO: 3) and rs1799963 (SEQ ID NO: 4). The AUC value increases from 0.6 to 0.63 (rs1799853; SEQ ID NO: 1) or from 0.6 to 0.62 (rs4379368; SEQ ID NO: 2) (Table 7).

Preferably, said method comprises determining in a sample from said woman subject the genotype of rs1799853 (SEQ ID NO: 1) and rs4379368 (SEQ ID NO: 2).

As shown in example 1, the determination of the genotype of rs1799853 (SEQ ID NO: 1) and rs4379368 (SEQ ID NO: 2) further improves the performance of the prognostic method compared to the standard genetic testing of rs6025 (SEQ ID NO: 3) and rs1799963 (SEQ ID NO: 4). The AUC value increases from 0.6 to 0.64 (rs1799853 and rs4379368) (Table 7).

In another embodiment, the invention also relates to a prognostic method for identifying if a subject undergoing a change in hormone levels is at risk of developing a blood clotting disease, the method comprising determining in a sample from said subject the genotype of at least one single nucleotide polymorphism (SNP) selected from the group consisting of rs1799853 (SEQ ID NO: 1) and/or rs4379368 (SEQ ID NO: 2), wherein said method further comprises determining the genotype of at least one single nucleotide polymorphism (SNP) selected from the group consisting of rs6025 (SEQ ID NO: 3), rs1799963 (SEQ ID NO: 4), rs8176719 (SEQ ID NO: 5), rs8176750 (SEQ ID NO: 6), rs9574 (SEQ ID NO: 7), rs2289252 (SEQ ID NO: 8), and rs710446 (SEQ ID NO: 9).

Preferably, the subject is a woman subject undergoing a change in hormone levels.

As shown in example 1, determining the genotype of rs1799853 (SEQ ID NO: 1), rs4379368 (SEQ ID NO: 2), rs6025 (SEQ ID NO: 3), rs1799963 (SEQ ID NO: 4), rs8176719 (SEQ ID NO: 5), rs8176750 (SEQ ID NO: 6), rs9574 (SEQ ID NO: 7), rs2289252 (SEQ ID NO: 8) and rs710446 (SEQ ID NO: 9) improves furthermore the prognostic method for identifying if a woman subject undergoing a change in hormone levels is at risk of developing a blood clotting disease. The AUC value increases from 0.6 to 0.7 (Table 7).

The determination of the genotype of rs1799853 (SEQ ID NO: 1) and/or rs4379368 (SEQ ID NO: 2) performed in addition to the determination of the genotype of a combination of SNPs consisting of rs6025, rs1799963, rs8176719, rs2066865 and rs2036914 (DeHaan H G., 2012) improves the prognostic method for identifying if a woman subject undergoing a change in hormone levels is at risk of developing a blood clotting disease. The AUC increases from 0.628 to 0.641 (Example 1, Table 8).

Diverse forms of variations in a DNA sequence exist. Single nucleotide polymorphisms (SNPs) are the most common ones, representing more than 90% of all differences among individuals. Precisely, a SNP is a commonly occurring DNA variation (e.g. with frequency higher than 1%) in which two chromosomes differ in a given segment at a single position (a single base pair). Though SNPs are naturally and commonly occurring variations in human DNA, if they are part of the coding or regulatory DNA sequences, they might actually alter the expression of genes or stability of its transcripts and thus confer some advantages and risk to the carriers. It is now well established that these common genetic variants or their combination might be associated to some major traits, such as diseases. SNPs are well known to person skilled in the art and are notably described in the NCBI database dbSNP (www.ncbi.nlm.nih.gov/SNP/).

As used herein, the main SNPs that are concerned by the invention are described as follows:

TABLE 1

| SEQ ID NO: | rs | Sequence | Gene |
|---|---|---|---|
| SEQ ID NO: 1 | rs1799853 | GATGGGGAAG AGGAGCATTG AGGAC[C/T] GTGTTCAAGA GGAAGCCCGC TGCCT | CYP2C9 gene (NG_008385) |

TABLE 1 -continued

| SEQ ID NO: | rs | Sequence | Gene |
|---|---|---|---|
| SEQ ID NO: 2 | rs4379368 | TGGATGGTAT TGACTTTTAC ATCAC[C/T] GAAGGTGTTT CCATAGATGG AAGAC | SUGCT gene (NG_023422) |
| SEQ ID NO: 3 | rs6025 | TGTAAGAGCA GATCCCTGGA CAGGC[A/G] AGGAATACAG GTATTTTGTC CTTGA | Factor V gene (NG_011806) |
| SEQ ID NO: 4 | rs1799963 | GTTCCCAATA AAAGTGACTC TCAGY[A/G] AGCCTCAATG CTCCCAGTGC TATTC | Factor H gene (NG_008953) |
| SEQ ID NO: 5 | rs8176719 | GCAGTAGGAA GGATGTCCTC GTGGT[-/G] ACCCCTTGGC TGGCTCCCAT TGTCT | ABO gene (NG_006669) |
| SEQ ID NO: 6 | rs8176750 | CCAAGAACCA CCAGGCGGTC CGGAA[-/C] CCGTGAGCGG CTGCCAGGGG CTCTG | ABO gene (NG_006669) |
| SEQ ID NO: 7 | rs9574 | GCGATGTTAA TTACTCTCCA GCCCC[C/G] TCAGAAGGGG CTGGATTGAT GGAGG | PROCR gene (NG_032899) |
| SEQ ID NO: 8 | rs2289252 | GTGAGGGTGA GGCTTGTCTC TCTCT[C/T] GCCCTCTCAT CCTGGCACAT GTGCG | Factor 11 gene (NG_008051) |
| SEQ ID NO: 9 | rs710446 | AGGGATCCAA TCGTCATCAC TCTGT[A/G] TGGGAGCTGG TGATATAGGA GGCAT | KNG1 gene (NG_016009) |

In the prognostic methods according to the invention, the genotype of the SNPs is determined by nucleic acid sequencing and/or by PCR analysis in a sample of the subject, preferably a woman subject undergoing a change in hormone levels.

The sample may be any biological sample, containing DNA and derived from the subject. This includes body fluids, tissues, cells, biopsies and so on. The preferred samples are saliva and blood.

The sample is collected according to the transfer method of choice and is treated to purify nucleic acids. These treatments include lysis, centrifugation and washing steps. The lysis includes mechanical, physical or chemical approaches. The purified nucleic acid is then used to genotype the above SNPs. The nucleic acid is added to a buffer, enzymes, specific primers and/or probes. This can be done in any suitable device such as tube, plate, well, glass etc. The genotype of the above SNPs may be detected by various methods including PCR, RFLP, allele-specific PCR, quantitative PCR, sequencing, microarray, and hybridization.

Sequencing can be performed using automatic sequencers using various techniques and following state of the art protocols. The sequencing reactions can be performed on complete genes or on specific regions covering the SNPs. For standard sequencing, the reaction requires a piece of DNA that initiates the amplification reaction, standard nucleotides and modified nucleotides that block the amplification reaction. Next generation sequencing can be performed by various techniques that massively amplified DNA regions.

Amplification can be performed using numerous techniques such as polymerase chain reaction (PCR), allele-specific PCR (ASA-PCR), PCR followed by a restriction enzyme digestion (RFLP-PCR) and quantitative PCR. These techniques are based on the amplification of specific regions using small pieces of DNA that hybridize to the specific regions and initiate the amplification reaction. The reaction also requires necessary components to make the amplification work such as nucleotides and enzymes. In the case of ASA-PCR, a multiplex reaction or independent reactions are used by mixing 4 pieces of DNA that will initiate the amplification reaction. Among these 4 pieces of DNA, 2 are specific to the SNP; one will be specific to the effect allele and the other will be specific to the non-effect allele. The sizes of the amplified regions would be different to be able to distinguish between them on a regular agarose gel. In the case of RFLP-PCR, the amplified material is treated using a restriction enzyme to cut the amplified region according to the SNP allele. For example, enzyme A would cut the effect allele, while it would not cut the non-effect allele. The sizes of the digested amplified region are distinguished on a regular agarose gel. For quantitative PCR, labelled probes specific to each allele are added to the amplification reaction to distinguish between the two alleles.

Genotyping can also be performed using hybridization techniques on a solid support or in suspension. These techniques are based on the hybridization of material amplified with allele specific probes and primers onto a support. The amplified material is labelled to distinguish the different alleles.

The term "effect allele" according to the invention refers to the allele that confers the risk and/or the protective effect to develop a blood clotting disease to a subject, preferably a woman subject undergoing a change in hormone levels. The term "effect allele", thus refers to a SNP or allele that is associated with high relative risk of developing a blood clotting disease.

The term "non-effect allele" refers to the allele that does not confer a risk nor a protective effect to develop a blood clotting disease to a subject, preferably a woman subject undergoing a change in hormone levels.

In the context of the invention, prognostic methods are performed to determine the presence or absence of homozygous or heterozygous forms of at least one "effect allele". The genotyping data include three possibilities, which are homozygous for the "effect-allele", heterozygous, or homozygous for the "non-effect allele".

Table 2 gives the detailed genotypes for each SNP (A: Adenine, G: Guanine, C: Cytosine, T: Thymine, -: deletion).

TABLE 2

| SNP | Homozygous for the "effect allele" | Hetero-zygous | Homozygous for the "non-effect allele" |
|---|---|---|---|
| rs1799853 | (T;T) | (C;T) | (C;C) |
| rs4379368 | (T;T) | (C;T) | (C;C) |
| rs6025 | (A;A) | (A;G) | (G;G) |
| rs1799963 | (A;A) | (A;G) | (G;G) |
| rs8176719 | (G;G) | (—;G) | (—;—) |
| rs8176750 | (—;—) | (—;C) | (C;C) |
| rs9574 | (G;G) | (C;G) | (C;C) |
| rs2289252 | (T;T) | (C;T) | (C;C) |
| rs710446 | (G;G) | (A;G) | (A;A) |

In the prognostic methods of the invention, the presence of allele T in rs1799853 (SEQ ID NO: 1) and/or allele T in rs4379368 (SEQ ID NO: 2) in heterozygous or homozygous form indicates that said subject has an increased risk of developing a blood clotting disease.

In comparison, the presence of allele C in rs1799853 (SEQ ID NO: 1) and/or allele C in rs4379368 (SEQ ID NO: 2) in homozygous form indicates that said subject has no increased risk of developing a blood clotting disease.

As shown in the examples, the presence of allele T in rs1799853 (SEQ ID NO: 1) in heterozygous or homozygous form in patients 11-14 and 31-32 indicates that these patients have an increased risk of developing a blood clotting disease. Similarly, the presence of allele T in rs4379368 (SEQ ID NO: 2) in heterozygous or homozygous form in patients 15-17 indicates that these patients have an increased risk of developing a blood clotting disease. Indeed, all these patients have developed DVT or PE (Examples 2-3, tables 9 and 11).

Preferably, the presence of allele T in rs1799853 (SEQ ID NO: 1) and allele T in rs4379368 (SEQ ID NO: 2) in heterozygous or homozygous form indicates that said subject has an increased risk of developing a blood clotting disease.

As shown in the examples, the presence of allele T in rs1799853 (SEQ ID NO: 1) and allele T in rs4379368 (SEQ ID NO: 2) in heterozygous or homozygous form in patients 18-24 and 33-36 indicates that these patients have an increased risk of developing a blood clotting disease. All these patients have developed DVT or PE. In contrast, patients 1-10 and 25-30 with allele C in rs1799853 (SEQ ID NO: 1) and allele C in rs4379368 (SEQ ID NO: 2) in homozygous form have not developed a blood clotting disease (Examples 2-3, tables 9 and 11).

More preferably, the presence of allele T in rs1799853 (SEQ ID NO: 1), and/or allele T in rs4379368 (SEQ ID NO: 2) and an allele in heterozygous or homozygous form in at least one SNP selected from the group comprising allele A in rs6025 (SEQ ID NO: 3), allele A in rs1799963 (SEQ ID NO: 4), allele G in rs8176719 (SEQ ID NO: 5), allele (–) in rs8176750 (SEQ ID NO: 6), allele G in rs9574 (SEQ ID NO: 7), allele T in rs2289252 (SEQ ID NO: 8), and allele G in rs710446 (SEQ ID NO: 9), indicate that said subject has an increased risk of developing a blood clotting disease.

As shown in example 4, the presence of allele T in rs1799853 (SEQ ID NO: 1) and/or allele T in rs4379368 (SEQ ID NO: 2) in heterozygous or homozygous form along with at least one SNP selected from the group comprising allele A in rs6025 (SEQ ID NO: 3), allele A in rs1799963 (SEQ ID NO: 4), allele G in rs8176719 (SEQ ID NO: 5), allele (–) in rs8176750 (SEQ ID NO: 6), allele G in rs9574 (SEQ ID NO: 7), allele T in rs2289252 (SEQ ID NO: 8), and allele G in rs710446 (SEQ ID NO: 9), in patients 44-51 indicate that these patients have an increased risk of developing a blood clotting disease. All these patients have developed DVT or PE. In contrast, patients 37-43 with allele C in rs1799853 (SEQ ID NO: 1) and/or allele C in rs4379368 (SEQ ID NO: 2) in homozygous form have not developed a blood clotting disease (Table 2 and Example 4, Table 12).

The present invention also relates to a prognostic method for identifying if a subject is at risk of developing a blood clotting disease, the method comprising the steps of:

a) determining in a sample from said subject the genotype of at least one single nucleotide polymorphism (SNP) selected from the group consisting of rs1799853 (SEQ ID NO: 1) and rs4379368 (SEQ ID NO: 2); and b) determining the clinical risk factors of said subject.

As shown in example 5, the presence of allele T in rs1799853 (SEQ ID NO: 1) and/or allele T in rs4379368 (SEQ ID NO: 2) in heterozygous or homozygous form along with clinical risk factors selected from the group comprising the smoking status, the BMI, the age, the familial history of blood clotting diseases and/or the change in hormone levels, in patients 58-63 indicate that these patients have an increased risk of developing a blood clotting disease. All these patients have developed DVT or PE. In contrast, patients 52-57 with allele C in rs1799853 (SEQ ID NO: 1) and allele C in rs4379368 (SEQ ID NO: 2) in homozygous form have not developed a blood clotting disease (Table 2 and Example 5, Table 13).

The invention further provides a prognostic method for identifying if a subject is at risk of developing a blood clotting disease, the method comprising the steps of:

a) determining in a sample from said subject the genotype of at least one single nucleotide polymorphism (SNP) selected from the group consisting of rs1799853 (SEQ ID NO: 1) and rs4379368 (SEQ ID NO: 2);

b) determining in said sample the genotype of at least one single nucleotide polymorphisms (SNPs) selected from the group comprising rs6025 (SEQ ID NO: 3), rs1799963 (SEQ ID NO: 4), rs8176719 (SEQ ID NO: 5), rs8176750 (SEQ ID NO: 6), rs9574 (SEQ ID NO: 7), rs2289252 (SEQ ID NO: 8), and rs710446 (SEQ ID NO: 9); and c) determining the clinical risk factors of said subject.

Preferably, the subject is a woman undergoing a change in hormone levels.

As shown in example 6, the presence of allele T in rs1799853 (SEQ ID NO: 1) and/or allele T in rs4379368 (SEQ ID NO: 2) in heterozygous or homozygous form and at least one single nucleotide polymorphisms (SNPs) selected from the group comprising rs6025 (SEQ ID NO: 3), rs1799963 (SEQ ID NO: 4), rs8176719 (SEQ ID NO: 5), rs8176750 (SEQ ID NO: 6), rs9574 (SEQ ID NO: 7), rs2289252 (SEQ ID NO: 8), and rs710446 (SEQ ID NO: 9), along with clinical risk factors selected from the group comprising the smoking status, the BMI, the age, the familial history of blood clotting diseases and/or the change in hormone levels, in patients 64-74 indicate that these patients have an increased risk of developing a blood clotting disease. All these patients have developed DVT or PE. In contrast, patients 75-81 with allele C in rs1799853 (SEQ ID NO: 1) and allele C in rs4379368 (SEQ ID NO: 2) in homozygous form have not developed a blood clotting disease (Table 14, Example 6).

Clinical risk factors are for example selected from the group comprising the smoking status, the BMI, the age, the familial history of blood clotting diseases, the change in hormone levels, the personal history of blood clotting diseases, the alcohol status, a personal history of hypertension, of cholesterol, of diabetes, of autoimmune disease, of cancer and of other cardiovascular diseases, the history of contraception, the duration of the contraception, and the concomitant use of other drugs. For example, clinical risk factors may be determined through the request form sent by the physician or healthcare provider.

Preferably, clinical risk factors are selected from the group comprising the smoking status, the BMI, the age, the familial history of blood clotting diseases and/or the change in hormone levels.

The invention also relates to prognostic methods as described above, wherein said woman subject undergoing a change in hormone levels is having a contraceptive, a combined contraceptive, a hormonal replacement therapy, a progestin-only contraceptive, is pregnant, is having assisted reproductive technology, or is in postpartum period.

The type of hormone present in the subject's treatment includes the progestins levonorgestrel, norgestimate, gestoden, desogestrel, drospirenone, dienogest, cyproterone acetate, in particular but not exclusively and also the estrogens estradiol, ethinylestradiol, estradiol acetate, estradiol cypionate, estradiol valerate, estradiol enanthate, estradiol benzoate, estradiol hemihydrate, in particular but not exclusively. It also includes progestin-only pills, intrauterine devices and hormone replacement therapy according to the route of administration such as oral or transdermal patch and other therapy such as Livial (Tibolone).

In the prognostic methods of the invention, blood-clotting diseases are selected from the group comprising deep vein thrombosis, pulmonary embolism, vein thrombosis and arterial thrombosis.

Preferably, the present invention provides prognostic methods for identifying if a woman subject undergoing a change in hormone levels is at risk of developing a deep vein thrombosis and/or a pulmonary embolism.

The invention further provides a kit for use in the prognostic methods described above, comprising:
i) Detection reagents for detecting SNP selected from the group consisting of rs1799853 (SEQ ID NO: 1) and/or rs4379368 (SEQ ID NO: 2); and optionally
ii) Instructions for use.

In a separate embodiment, a kit for use in the prognostic methods described above comprises:
i) Detection reagents for detecting SNP selected from the group consisting of rs6025 (SEQ ID NO: 3), rs1799963 (SEQ ID NO: 4), rs8176719 (SEQ ID NO: 5), rs8176750 (SEQ ID NO: 6), rs9574 (SEQ ID NO: 7), rs2289252 (SEQ ID NO: 8), rs710446 (SEQ ID NO: 9), rs4379368 (SEQ ID NO: 2) and rs1799853 (SEQ ID NO: 1); and optionally
ii) Instructions for use.

In particular, the kit contains necessary components to genotype the SNPs selected from the group comprising of rs1799853 (SEQ ID NO: 1), rs4379368 (SEQ ID NO: 2), rs6025 (SEQ ID NO: 3), rs1799963 (SEQ ID NO: 4), rs8176719 (SEQ ID NO: 5), rs8176750 (SEQ ID NO: 6), rs9574 (SEQ ID NO: 7), rs2289252 (SEQ ID NO: 8), and rs710446 (SEQ ID NO: 9). These components include primers and/or probes specific to each SNP. The primers are necessary to initiate the amplification of each specific region corresponding to each SNP. The probes hybridize specifically to each allele of each SNP and allow the detection of each allele. The probes for each allele can be labelled with different fluorophores to allow distinct detection. The kit can also contain solid support to hybridize amplified material and allow the detection of each allele on the solid support after labelling reaction. The kit can also contain necessary reagents to sequence the regions around the 9 SNPs listed above or the full corresponding genes. These reagents include specific primers for each primer that would allow initiating the amplification reaction and modified nucleotides.

Preferably, the SNP detection reagent is an isolated or synthetic DNA oligonucleotide probe or primer, or a RNA oligonucleotide or primer or a PNA oligomer or a combination thereof, that hybridizes to a fragment of a target nucleic acid molecule containing one of the SNPs specified in any one of SEQ ID Nos. 1 to 9, or a complement thereof.

In particular, said SNP detection reagent can differentiate between nucleic acids having a particular nucleotide at a target SNP position.

In the present invention, the SNP detection reagent hybridizes under stringent conditions to at least 8, 10, 12, 16, 18, 20, 22, 25, 30, 40, 50, 55, 60, 65, 70, 80, 90, 100, 120 or more consecutive nucleotides in a target nucleic acid molecule comprising at least one of the SNPs specified in any one of SEQ ID Nos. 1 to 9, or a complement thereof.

Preferably, according to the invention, at least one SNP detection reagent in the kit is an oligonucleotide or primer having a length of at least 8 nucleotides, preferably a length of at least 10, 12, 16, 17, 18, 19, 20, 21, 22, 23, 24 or 25 nucleotides.

The invention also relates to a kit for use, wherein the SNP detection reagent is a compound that is labelled.

The present invention further relates to a computer program or a computer-readable media containing means for carrying out a prognostic method for identifying if a subject is at risk of developing a blood clotting disease, the method comprises determining in a sample from said subject the genotype of at least one single nucleotide polymorphism (SNP) selected from the group consisting of rs1799853 (SEQ ID NO: 1) and rs4379368 (SEQ ID NO: 2).

Preferably, said method further comprises the step of determining the genotype of at least one single nucleotide polymorphism (SNP) selected from the group consisting of rs6025 (SEQ ID NO: 3), rs1799963 (SEQ ID NO: 4), rs8176719 (SEQ ID NO: 5), rs8176750 (SEQ ID NO: 6), rs9574 (SEQ ID NO: 7), rs2289252 (SEQ ID NO: 8), and rs710446 (SEQ ID NO: 9).

The above-described methods may further comprises the step of determining the clinical risk factors of said subject.

In a separate embodiment, the present invention further relates to a computer program or a computer-readable media containing means for carrying out a prognostic method for identifying if a woman undergoing a change in hormone levels is at risk of developing a blood clotting disease, the method comprises determining in a sample from said woman the genotype of at least one single nucleotide polymorphism (SNP) selected from the group consisting of rs1799853 (SEQ ID NO: 1) and rs4379368 (SEQ ID NO: 2).

Preferably, said method further comprises the step of determining the genotype of at least one single nucleotide polymorphism (SNP) selected from the group consisting of rs6025 (SEQ ID NO: 3), rs1799963 (SEQ ID NO: 4), rs8176719 (SEQ ID NO: 5), rs8176750 (SEQ ID NO: 6), rs9574 (SEQ ID NO: 7), rs2289252 (SEQ ID NO: 8), and rs710446 (SEQ ID NO: 9).

The above-described methods may further comprises the step of determining the clinical risk factors of said woman undergoing a change in hormone levels.

Thus, the present invention relates to a computer program or a computer-readable media containing means for carrying out a prognostic method for identifying if a woman undergoing a change in hormone levels is at risk of developing a blood clotting disease, the method comprising the steps of:
a) determining in a sample from said subject the genotype of at least one single nucleotide polymorphism (SNP) selected from the group consisting of rs1799853 (SEQ ID NO: 1) and rs4379368 (SEQ ID NO: 2);
b) determining in said sample the genotype of at least one single nucleotide polymorphisms (SNPs) selected from the group comprising rs6025 (SEQ ID NO: 3), rs1799963 (SEQ ID NO: 4), rs8176719 (SEQ ID NO: 5), rs8176750 (SEQ ID NO: 6), rs9574 (SEQ ID NO: 7), rs2289252 (SEQ ID NO: 8), and rs710446 (SEQ ID NO: 9); and
c) determining the clinical risk factors of said subject.

Further SNPs can be determined based on the SNPs described in the present invention by statistical correlation. "Linkage disequilibrium" (LD) refers to the statistical correlation between two neighboring SNPs. LD is generally quantified with either Lewontin's parameter of association (Lewontin, R. C. (1964). Genetics. 49 (1): 49-67) or with the $r^2$ parameter based on Pearson correlation coefficient (Karl Pearson (1895) Proceedings of the Royal Society of London, 58: 240-242). When the LD value is equal to 1, the two SNPs are in complete disequilibrium. In contrast, two SNPs with a LD value equal to 0 are in complete linkage equilibrium. Linkage disequilibrium is calculated following the application of the expectation maximization algorithm (EM) for the estimation of haplotype frequencies.

Thus, in the present invention, SNPs considered in LD with rs1799853 (SEQ ID NO: 1), rs4379368 (SEQ ID NO: 2), rs6025 (SEQ ID NO: 3), rs1799963 (SEQ ID NO: 4), rs8176719 (SEQ ID NO: 5), rs8176750 (SEQ ID NO: 6), rs9574 (SEQ ID NO: 7), rs2289252 (SEQ ID NO: 8), or rs710446 (SEQ ID NO: 9) are SNPs with a $r^2$ greater than 0.5.

In another separate embodiment, the present invention relates to a prognostic method for identifying if a subject is at risk of developing a blood clotting disease, the method comprising:
a) Obtaining a biological sample from a subject;
b) Determining from said sample the genotype of at least one single nucleotide polymorphism selected from the group consisting of rs1799853 (SEQ ID NO: 1) and rs4379368 (SEQ ID NO: 2);
c) Prognosing the subject with high risk of developing a blood clotting disease when allele T in rs1799853 (SEQ ID NO: 1) and/or allele T in rs4379368 (SEQ ID NO: 2) in heterozygous or homozygous form is/are detected; and
d) Administering an effective amount of a compound adapted to the prevention of a blood clotting disease to said subject.

Compounds adapted to the prevention of a blood clotting disease are selected from the group comprising Apixaban, Rivaroxaban, Dabigatran, Edoxaban, heparin, vitamin K antagonists and coumarin drugs such as Warfarin.

The present invention relates also to a method of treatment of a subject having a blood clotting disease, the method comprising:
a) Obtaining a biological sample from a subject;
b) Determining from said sample the genotype of at least one single nucleotide polymorphism selected from the group consisting of rs1799853 (SEQ ID NO: 1) and rs4379368 (SEQ ID NO: 2);
c) Diagnosing the subject with high risk of developing a blood clotting disease when allele T in rs1799853 (SEQ ID NO: 1) and/or allele T in rs4379368 (SEQ ID NO: 2) in heterozygous or homozygous form is/are detected; and
d) Administering an effective amount of a compound adapted to the treatment of a blood clotting disease to said subject.

Compounds adapted to the treatment of a blood clotting disease are selected from the group comprising Apixaban, Rivaroxaban, Dabigatran, Edoxaban, heparin, vitamin K antagonists and coumarin drugs such as Warfarin.

Preferably, the subject is a woman undergoing a change in hormone levels.

Those skilled in the art will appreciate that the invention described herein is susceptible to variations and modifications other than those specifically described. It is to be understood that the invention includes all such variations and modifications without departing from the spirit or essential characteristics thereof. The invention also includes all of the steps, features, compositions and compounds referred to or indicated in this specification, individually or collectively, and any and all combinations or any two or more of said steps or features. The present disclosure is therefore to be considered as in all aspects illustrated and not restrictive, the scope of the invention being indicated by the appended Claims, and all changes that come within the meaning and range of equivalency are intended to be embraced therein.

Various references are cited throughout this specification, each of which is incorporated herein by reference in its entirety.

The foregoing description will be more fully understood with reference to the following Examples. Such examples, are, however, exemplary of methods of practising the present invention and are not intended to limit the scope of the invention.

EXAMPLE

Example 1: Performance of the Prognostic Method

Characteristics of the Studied Population

This study involved human subjects and was carried out in accordance with the tenets of the Declaration of Helsinki; all participants signed an informed consent. The study includes 794 female cases who have developed at least one episode of VTE while taking CC. These cases are part of the previously described PIL1 Genetic RIsk Monitoring (PIL-GRIM) study (Suchon P, et al. (2017) Clin Genet; 91(1): 131-36), which relates the method used to confirm the occurence of thrombosis. 828 control women were also collected from different sources: 523 are part of the PIL-GRIM study; 174 are part of the CoLaus study (Firmann M, et al. (2008) BMC Cardiovasc Disord; 8:6), 56 were recruited between 1997 and 1998 in south of France and the remaining controls were recruited between 2012 and 2016 among Swiss population. These control women are taking CC but have not developed VTE by the time of the genotyping investigation.

Among 1622 women taking an oral contraceptive pill, 794 have developed a thrombotic event, either a deep vein thrombosis (DVT) or a pulmonary embolism (PE). Distribution of age, BMI and smoking status are presented in both populations (Tables 3 and 4). Age distribution is similar in both groups, BMI and Smoking status are slightly higher in cases.

TABLE 3

| Clinical characteristics | Subject (n = 794) | Controls (n = 828) |
|---|---|---|
| Age (years) | 32.3 | 31.5 |
| Body Mass Index (kg/m2) | 24 | 22.3 |
| Smoking status | 260 | 206 |

TABLE 4

|  | Cases (n) | Controls (n) |
|---|---|---|
| Total number | 794 | 828 |
| VTE | 794 |  |
| DVT | 600 |  |
| PE | 194 |  |
| Age (mean) | 32 | 31.5 |
| BMI (mean) | 24 | 23 |
| Family history of VTE | 222 | 19 |
| Smoking | 260 | 206 |

Genotyping 50 genetic polymorphisms were identified for all 1622 women in the study using Illumina's Veracode-BeadXpress technology. The selection of these SNPs to be tested was made according to the meta-analyses of the existing literature and the laboratory studies that were performed. In more details, SNPs were genotyped using Illumina GoldenGate technology and assessed using Illumina BeadXpress and GenomeStudio V2011.1 software. Clusters for each SNP were curated manually and undetermined samples were further genotyped using Sanger sequencing. SNP rs1053878 was genotyped using RFLP-PCR; in more details, the DNA region was amplified with the following primers (Forward: 5'-GCCACCGTGTCCACTACTATG-3' (SEQ ID NO: 10) and Reverse: 5'-GTCCACGCACACCAGGTAAT-3' (SEQ ID NO: 11)) and the amplicons were digested with PvuII restriction enzyme. Controls from the CoLaus cohort were previously genotyped as described (Kutalik Z, et al. (2011) Biostatistics; 12(1):1-17). For the CoLaus controls, proxys (r2>85%) were used for 9 SNPs (rs4572916 for rs10029715, rs8176704 for rs1053878, rs3736455 for rs13146272, rs6018 for rs1800595, rs4253417 for rs2289252, rs11038993 for rs3136516, rs2169682 for rs7082872, rs687621 for rs8176719 and rs2069952 for rs9574). The quality of the genotyping data was assessed by GenomeStudio and by visual inspection. Genotyping data were validated by sequencing or RFLP-PCR.

Statistical Analyses

The cohort was randomly divided into a training set and a test set of equal size. The training set was used to perform a stepwise selection (AIC, Akaike information criterion) and a logistic regression to generate coefficients. The fitted model was then applied to the test dataset to compute predictions. This process was repeated 10,000 times and the medians of the coefficients were used. The variables not selected in the run were assigned a null coefficient.

The Odd-Ratio (OR) quantifies the association between two parameters in a given population (Cornfield J., (1951). Journal of the National Cancer Institute. 11: 1269-1275). These values are obtained from mathematical models such as the logistic regression used herein. A logistic regression is a mathematical model that measures the relationship between variables by predicting the probability of a given outcome (Walker, S. H.; Duncan, D. B. (1967). Biometrika. 54: 167-178). The OR and p-values are the output of the logistic regression and correspond to the strength and the significance of the measured relationship respectively.

Results

Logistic regression models were fitted step-wise to find the optimal multivariate model in the 10,000 training sets. By averaging these 10,000 models, we identified 9 out of the 46 tested SNPs that were in the averaged model and also significantly associated with the development of thrombosis (Table 5).

This approach confirmed the association between DVT and/or PE with a number of SNPs already described in the literature (Table 5). The table includes the Odd-Ratio (OR) observed in the literature, the literature references and the p-value obtained from the present described study. The Odd-Ratio indicates the association between a SNP and the development of thrombosis.

TABLE 5

| SNP | Gene | Non-effect allele > effect allele | OR[1] | References[2] | p-value[3] |
|---|---|---|---|---|---|
| rs6025 (SEQ ID NO: 3) | Factor V gene (NG_011806) | G > A | 4.3 | De Haan, 2012 | $8.3 \times 10^{-14}$ |
| rs1799963 (SEQ ID NO: 4) | Factor II gene (NG_008953) | G > A | 3 | De Haan, 2012 | $3.7 \times 10^{-8}$ |
| rs8176719 (SEQ ID NO: 5) | ABO gene (NG_006669) | — > G | 1.74 | De Haan, 2012 | $6.0 \times 10^{-7}$ |
| rs8176750 (SEQ ID NO: 6) | ABO gene (NG_006669) | C > — | 1.89-1.91 | Tregouet, 2009 | $2.5 \times 10^{-3}$ |
| rs9574 (SEQ ID NO: 7) | PROCR gene (NG_032899) | C > G | 1.18[+] | De Haan, 2012 | $9 \times 10^{-4}$ |
| rs2289252 (SEQ ID NO: 8) | Factor 11 gene (NG_008051) | C > T | 1.36 | De Haan, 2012 | $2.9 \times 10^{-4}$ |
| rs710446 (SEQ ID NO: 9) | KNG1 gene (NG_016009) | A > G | 1.196 | Morange, 2011 | $3.8 \times 10^{-2}$ |

[1]Odd-Ratio, for the association between the SNP and the development of thrombosis, obtained from the literature. Most of these OR are based on MARTHA cohort.
[+]This OR corresponds to the SNP rs867186. Both rs9574 and rs867186 are part of the haplotype A2 and A3 that are associated with the risk of thrombosis.
[2]References for the related OR
[3]p-values obtained from the cohort of 1622 women and a logistic regression on the whole population Significant p-values were also obtained for two additional SNPs that were not previously associated with the development of thromboembolic events. These two SNPs are described in Table 6.

TABLE 6

| SNP | Gene | Non-effect allele > effect allele | p-value[1] | OR[2] |
|---|---|---|---|---|
| rs1799853 (SEQ ID NO: 1) | CYP2C9 gene (NG_008385) | C > T | $5.0 \times 10^{-4}$ | 1.55 |
| rs4379368 (SEQ ID NO: 2) | SUGCT gene (NG_023422) | C > T | $3.6 \times 10^{-2}$ | 1.35 |
| rs1057910 | CYP2C9 gene (NG_083805) | A > C | >0.05 | — |
| rs35599367 | CYP3A4 gene (NG_008421) | C > T | >0.05 | — |

[1] p-values obtained from the cohort of 1622 women and a logistic regression on the whole population
[2] Odd-Ratio obtained from the cohort of 1622 women and a logistic regression Different approaches can be used to generate p-values. In tables 4 and 5, the p-values have been determined from 10,000 repetitions of a logistic regression using the whole 1622 women population whilst other approaches generate p-values using a logistic regression only on half of the population randomly selected 10,000 times in an out-of-sample manner.

rs1799853 (SEQ ID NO: 1) is present in the gene coding for the cytochrome CYP2C9. This SNP is also known as the allele*2 in official nomenclature for the CYP450 enzymes. This variant is associated with a strong diminution of the enzyme's activity (Thijssen H. H., (2005), Clin Pharmacol Ther., 74, 61-68). Ethinylestradiol that is the estrogen present in most of CC is metabolised via CYP450 pathways. Several of the cytochromes are involved including CYP2C9 (Lee A J., (2003), Endocrinology, 144(8):3382-98). Other SNPs associated with the activity of several cytochromes involved in the metabolism of estrogen have been tested (e.g. rs1057910 and rs35599367, Table 6). However, no statistically significant association with the development of VTE in CC users was found. The same genetic variant was also identified as one of the factors impairing elimination of anticoagulant drugs derived from coumarine (Rettie A E., Tai G., (2006), The pharmocogenomics of warfarin: closing in on personalized medicine. Mol Interv 6: 223-227). The other genetic variants, such as CYP2C9*3 (rs1057910, Table 6) were demonstrated to have the same effect on the drug metabolism. CYP2C9*3 was tested, but it had no statistically significant association with the development of VTE in CC users.

rs4379368 (SEQ ID NO: 2) is present in the gene sequence coding for the succinyl-CoA:glutarate-CoA transferase. This SNP was initially found to be associated with migraine (Anttila V, (2013) Nat. Gen., 45(8):912-7). Other SNPs associated with the development of migraine have been tested (e.g. rs2651899 and rs10915437). However, no statistically significant association with the development of VTE in CC users was found.

Receiver Operating Characteristic (ROC) curve was established and measures how well the different models discriminate the women at risk to the women without risk. The true positive rate (TPR) is plotted against the false positive rate (FPR) at various threshold settings (Fawcett T., (2006), Pattern Recognition Letters., 27: 861-874).

The Area Under the Curve (AUC) is equal to the probability that a positive test ranks higher than a negative test in order to discriminate the women at risk to the women without risk. The AUC ranges from 0.5 (50%—no predictive value) to 1 (100%—perfect discrimination; Fawcett T., (2006), Pattern Recognition Letters., 27: 861-874).

The AUC obtained following the logistic regression described herein and corresponding to the different combinations of SNPs are shown in table 7. There are several ways to calculate AUC, either using the whole 1622 women population or using only the test set that corresponds to half of the population that was not used to select variables. The AUC presented in table 7 have been calculated using the whole 1622 women population.

TABLE 7

| rs and SEQ ID NO: | AUC |
|---|---|
| rs6025 (SEQ ID NO: 3) | 0.60 |
| rs1799963 (SEQ ID NO: 4) | |
| rs6025 (SEQ ID NO: 3) | 0.63 |
| rs1799963 (SEQ ID NO: 4) | |
| rs1799853 (SEQ ID NO: 1) | |
| rs6025 (SEQ ID NO: 3) | 0.62 |
| s1799963 (SEQ ID NO: 4) | |
| rs4379368 (SEQ ID NO: 2) | |
| rs6025 (SEQ ID NO: 3) | 0.64 |
| rs1799963 (SEQ ID NO: 4) | |
| s1799853 (SEQ ID NO: 1) | |
| rs4379368 (SEQ ID NO: 2) | |
| rs6025 (SEQ ID NO: 3) | 0.70 |
| rs1799963 (SEQ ID NO: 4) | |
| rs8176719 (SEQ ID NO: 5) | |
| rs8176750 (SEQ ID NO: 6) | |
| rs9574 (SEQ ID NO: 7) | |
| s2289252 (SEQ ID NO: 8) | |
| rs710446 (SEQ ID NO: 9) | |
| rs4379368 (SEQ ID NO: 2) | |
| rs1799853 (SEQ ID NO: 1) | |

The values of the AUC demonstrate that rs4379368 (SEQ ID NO: 2), and/or rs1799853 (SEQ ID NO: 1) can be used in a prognostic method for identifying if a woman subject undergoing a change in hormone levels is at risk of developing a blood clotting disease. The determination of either rs4379368 (SEQ ID NO: 2), or rs1799853 (SEQ ID NO: 1) or both improves the performance of detection of women at risk compared to the standard genetic testing (rs6025 (SEQ ID NO: 3) and rs1799963 (SEQ ID NO: 4).

In addition to rs4379368 (SEQ ID NO: 2), and/or rs1799853 (SEQ ID NO: 1), testing rs6025 (SEQ ID NO: 3), rs1799963 (SEQ ID NO: 4), rs8176719 (SEQ ID NO: 5), rs8176750 (SEQ ID NO: 6), rs9574 (SEQ ID NO: 7), rs2289252 (SEQ ID NO: 8), rs710446 (SEQ ID NO: 9) further improves the prognostic method for identifying if a woman subject undergoing a change in hormone levels is at risk of developing a blood clotting disease.

Similarly, the addition of rs1799853 (SEQ ID NO: 1) and/or rs4379368 (SEQ ID NO: 2) to previously reported combination of SNP for identifying the risk of developing a blood clotting disease (DeHaan H G., (2012), Blood, 120: 656-663) increases the AUC when calculated using the whole 1622 women population. The combination of the 5 SNPs reported by DeHaan (rs6025, rs1799963, rs8176719, rs2066865 and rs2036914) reaches an AUC of 0.628 (Table 8, DeHaan). This AUC is improved when adding rs1799853 (SEQ ID NO: 1) or rs4379368 (SEQ ID NO: 2) or both.

TABLE 8

| rs and SEQ ID NO: | AUC |
|---|---|
| rs6025, rs1799963, rs8176719, rs2066865 and rs2036914 | 0.628 |
| rs6025, rs1799963, rs8176719, rs2066865 and rs2036914 + SEQ ID NO: 1 | 0.636 |
| rs6025, rs1799963, rs8176719, rs2066865 and rs2036914 + SEQ ID NO: 2 | 0.631 |
| rs6025, rs1799963, rs8176719, rs2066865 and rs2036914 + SEQ ID NO: 1 + SEQ ID NO: 2 | 0.641 |

Example 2: Determination of the Risk for Women Under Hormonal Contraceptives

The presence of rs1799853 (SEQ ID NO: 1) and/or rs4379368 (SEQ ID NO: 2) has been determined in a group of patients including women under hormonal contraceptives (Table 9). For each patient, the genotype of SEQ ID NO: 1, of SEQ ID NO: 2 and the family history has been indicated by values as follows:

Value of SEQ ID NO: 1-2 is 2=homozygous for the effect allele, 1=heterozygous for the effect allele, 0=homozygous for the non-effect allele.

Family history: 0=no family history of blood clotting disease, 1=family history (first grade) of blood clotting disease.

The development of a deep vein thrombosis (DVT) or a pulmonary embolism (PE) is indicated for each patient.

TABLE 9

| Patient No. | SEQ ID NO: 1 | SEQ ID NO: 2 | Family history | Development of DVT/PE |
|---|---|---|---|---|
| 1 | 0 | 0 | 0 | none |
| 2 | 0 | 0 | 1 | none |
| 3 | 0 | 0 | 0 | none |
| 4 | 0 | 0 | 0 | none |
| 5 | 0 | 0 | 0 | none |
| 6 | 0 | 0 | 1 | none |
| 7 | 0 | 0 | 0 | none |
| 8 | 0 | 0 | 0 | none |
| 9 | 0 | 0 | 0 | none |
| 10 | 0 | 0 | 1 | none |
| 11 | 1 | 0 | 1 | PE |
| 12 | 1 | 0 | 0 | DVT |
| 13 | 1 | 0 | 0 | DVT |
| 14 | 2 | 0 | 0 | DVT |
| 15 | 0 | 1 | 0 | DVT |
| 16 | 0 | 1 | 1 | DVT |
| 17 | 0 | 2 | 0 | DVT |
| 18 | 1 | 1 | 0 | DVT |
| 19 | 1 | 1 | 0 | DVT |
| 20 | 1 | 1 | 0 | DVT |
| 21 | 1 | 1 | 0 | DVT |
| 22 | 1 | 1 | 1 | DVT |
| 23 | 1 | 1 | 0 | PE |
| 24 | 1 | 1 | 1 | DVT |

The presence of SEQ ID NO: 1 in patients No. 11-14 is associated with the occurrence of blood clotting diseases such as DVT and PE. Similarly, the presence of SEQ ID NO: 2 in patients No. 15-17 is associated with the occurrence of blood clotting diseases such as DVT and PE. The presence of both SEQ ID NO: 1 and 2 in patients 18-24 is associated with DVT and PE. In contrast, patients No. 1 to 10 that are homozygous for the non-effect allele of SEQ ID NO: 1 and SEQ ID NO: 2 have not developed a blood clotting disease.

Example 3: Determination of the Risk for Men

Characteristics of the Studied Population

Among 36 men, 19 have developed a thrombotic event, either a deep vein thrombosis (DVT) or a pulmonary embolism (PE). Distribution of age, BMI and smoking status are presented in both populations (Table 10). Age distribution, BMI and Smoking status are similar in both group.

TABLE 10

| Clinical characteristics (mean) | Subjects (n = 17) | Controls (n = 19) |
|---|---|---|
| Age (years) | 44.5 | 47.5 |
| Body Mass Index (kg/m2) | 27 | 25 |
| Smoking status | 6 | 4 |

The presence of rs1799853 (SEQ ID NO: 1) and/or rs4379368 (SEQ ID NO: 2) has been determined in a group of patients including men (Table 11).

For each patient, the genotype of SEQ ID NO: 1 and SEQ ID NO:2 has been indicated by values as follows:

Value of SEQ ID NO: 1-2 is 2=homozygous for the effect allele, 1=heterozygous for the effect allele, 0=homozygous for the non-effect allele.

The development of a deep vein thrombosis (DVT) or a pulmonary embolism (PE) is indicated for each patient.

TABLE 11

| Patient No. | SEQ ID NO: 1 | SEQ ID NO: 2 | Development of DVT/PE |
|---|---|---|---|
| 25 | 0 | 0 | none |
| 26 | 0 | 0 | none |
| 27 | 0 | 0 | none |
| 28 | 0 | 0 | none |
| 29 | 0 | 0 | none |
| 30 | 0 | 0 | none |
| 31 | 1 | 0 | PE |
| 32 | 2 | 0 | DVT |
| 33 | 1 | 1 | DVT |
| 34 | 1 | 1 | DVT |
| 35 | 1 | 1 | DVT |
| 36 | 1 | 1 | DVT |

The presence of rs1799853 (SEQ ID NO: 1) and/or rs4379368 (SEQ ID NO: 2) in patients No. 31-36 is associated with the occurrence of blood clotting diseases such as DVT and PE in men. In contrast, patients No. 25-30 have not developed a blood clotting disease Example 4: Determination of the Risk Including a Combination of SNPs The presence of rs1799853 (SEQ ID NO: 1) and/or rs4379368 (SEQ ID NO: 2) has been determined in a group of patients along with an allele in heterozygous or homozygous form in at least one SNP selected from the group comprising allele A in rs6025 (SEQ ID NO: 3), allele A in rs1799963 (SEQ ID NO: 4), allele G in rs8176719 (SEQ ID NO: 5), allele (–) in rs8176750 (SEQ ID NO: 6), allele G in rs9574 (SEQ ID NO: 7), allele T in rs2289252 (SEQ ID NO: 8), and allele G in rs710446 (SEQ ID NO: 9) (Table 12).

For each patient, the genotype of SEQ ID NO: 1 and SEQ ID NO: 2 has been indicated by values as follows:

Value of SEQ ID NO: 1-9 is 2=homozygous for the effect allele, 1=heterozygous for the effect allele, 0=homozygous for the non-effect allele.

The development of a deep vein thrombosis (DVT) or a pulmonary embolism (PE) is indicated for each patient.

The gender of each patient is indicated as M for men and F for women.

TABLE 12

| Patient No. | 1 | 2 | 3 | 4 | 5 | 6 | 7 | 8 | 9 | DVT/PE | Gender |
|---|---|---|---|---|---|---|---|---|---|---|---|
| 37 | 0 | 0 | 1 | 0 | 1 | 0 | 1 | 0 | 1 | none | F |
| 38 | 0 | 0 | 0 | 1 | 1 | 1 | 1 | 0 | 0 | none | F |
| 39 | 0 | 0 | 0 | 1 | 1 | 0 | 1 | 1 | 0 | none | F |
| 40 | 0 | 0 | 0 | 0 | 0 | 0 | 1 | 2 | 2 | none | M |
| 41 | 0 | 0 | 0 | 0 | 1 | 0 | 0 | 0 | 0 | none | M |
| 42 | 0 | 0 | 0 | 0 | 1 | 0 | 1 | 0 | 0 | none | M |
| 43 | 0 | 0 | 0 | 0 | 1 | 0 | 1 | 0 | 1 | none | M |
| 44 | 1 | 0 | 0 | 0 | 2 | 0 | 1 | 2 | 0 | DVT | M |
| 45 | 2 | 0 | 0 | 0 | 2 | 0 | 1 | 1 | 2 | PE | M |
| 46 | 1 | 0 | 0 | 1 | 1 | 0 | 1 | 2 | 2 | PE | F |
| 47 | 1 | 0 | 1 | 0 | 1 | 0 | 0 | 1 | 2 | DVT | F |
| 48 | 1 | 1 | 0 | 1 | 0 | 0 | 1 | 1 | 0 | DVT | M |
| 49 | 1 | 1 | 0 | 0 | 1 | 0 | 1 | 0 | 0 | DVT | M |
| 50 | 1 | 1 | 1 | 0 | 1 | 0 | 1 | 2 | 2 | DVT | F |
| 51 | 1 | 1 | 1 | 0 | 1 | 0 | 0 | 0 | 2 | DVT | F |

Example 5: Determination of the Risk Including rs1799853 (SEQ ID NO: 1) and/or rs4379368 with Clinical Parameters The presence of rs1799853 (SEQ ID NO: 1) and/or rs4379368 (SEQ ID NO: 2) has been determined in a group of patients along with clinical parameters (Table 13).

For each patient, the family history, the BMI, the age, the smoking status and the genotype of SEQ ID NO: 1-2 has been indicated by values as follows:

Value of SEQ ID NO: 1-2 is 2=homozygous for the effect allele, 1=heterozygous for the effect allele, 0=homozygous for the non-effect allele.

Family history is 0=no family history of blood clotting disease, 1=family history (first grade) of blood clotting disease.

Smoking status is 0=no smoking; 1=current smoker.

The development of a deep vein thrombosis (DVT) or a pulmonary embolism (PE) is indicated for each patient as well as the gender, M for men and F for women.

TABLE 13

| Patient No | SEQ ID NO:1 | SEQ ID NO:2 | Familial History | BMI | Age | Smoking | Development of DVT/PE | Gender |
|---|---|---|---|---|---|---|---|---|
| 52 | 0 | 0 | 0 | 30.1 | 46 | 0 | none | M |
| 53 | 0 | 0 | 0 | 40 | 36 | 1 | none | M |
| 54 | 0 | 0 | 0 | 21.1 | 24 | 0 | none | M |
| 55 | 0 | 0 | 0 | 21.8 | 19 | 1 | none | F |
| 56 | 0 | 0 | 0 | 23 | 42 | 0 | none | F |
| 57 | 0 | 0 | 0 | 22.5 | 42 | 0 | none | F |
| 58 | 2 | 0 | 0 | 21 | 41 | 0 | DVT | M |
| 59 | 1 | 0 | 0 | 27.7 | 75 | 0 | PE | M |
| 60 | 2 | 0 | 0 | 20.8 | 29 | 0 | DVT | F |
| 61 | 0 | 1 | 0 | 29 | 22 | 1 | PE | F |
| 62 | 1 | 1 | 1 | 24 | 54 | 0 | DVT | M |
| 63 | 1 | 1 | 0 | 18.9 | 19 | 1 | DVT | F |

Example 6: Determination of the Risk Including a Combination of 9 SNPs with Clinical Parameters The genotype of SEQ ID NO: 1 to SEQ ID NO: 9 and various clinical parameters have been determined in a group of patients including women under hormonal contraceptives (Table 14). For each patient, the family history, the BMI, the age, the smoking status, and the genotype of SEQ ID NO: 1 to SEQ ID NO: 9 has been indicated by values as follows:

Family history: 0=no family history of blood clotting disease, I=family history (first grade) of blood clotting disease.

Smoking status: 0 corresponds to a non-smoking subject and 1 corresponds to a smoking subject.

Value of SEQ ID NO: 1 to SEQ ID NO: 9 is 2=homozygous for the effect allele, 1=heterozygous for the effect allele, 0=homozygous for the non-effect allele.

The development of a deep vein thrombosis (DVT) or a pulmonary embolism (PE) is indicated for each patient.

TABLE 14

| | SEQ ID NO: | | | | | | | | | Clinical Parameters | | | | |
| Patient | 1 | 2 | 3 | 4 | 5 | 6 | 7 | 8 | 9 | Family History | BMI | Age | Smoking | Development of: |
|---|---|---|---|---|---|---|---|---|---|---|---|---|---|---|
| 64 | 1 | 0 | 0 | 1 | 1 | 0 | 1 | 2 | 2 | 1 | 22.79 | 34 | 1 | PE |
| 65 | 1 | 0 | 1 | 0 | 1 | 0 | 0 | 1 | 2 | 0 | 27.92 | 48 | 0 | DVT |
| 66 | 1 | 0 | 0 | 1 | 2 | 0 | 0 | 1 | 2 | 0 | 20.31 | 38 | 0 | DVT |
| 67 | 2 | 0 | 1 | 0 | 1 | 0 | 1 | 1 | 1 | 0 | 20.83 | 29 | 0 | DVT |
| 68 | 2 | 0 | 0 | 1 | 1 | 0 | 2 | 2 | 1 | 0 | 24.14 | 19 | 0 | DVT |

TABLE 14-continued

| | | | | | | | | | | Clinical Parameters | | | |
|---|---|---|---|---|---|---|---|---|---|---|---|---|---|
| | SEQ ID NO: | | | | | | | | | Family | | | |
| Patient | 1 | 2 | 3 | 4 | 5 | 6 | 7 | 8 | 9 | History | BMI | Age | Smoking | Development of: |
| 69 | 0 | 1 | 1 | 0 | 2 | 0 | 1 | 1 | 1 | 0 | 23.05 | 24 | 1 | DVT |
| 70 | 0 | 1 | 1 | 0 | 1 | 0 | 0 | 1 | 1 | 0 | 28.93 | 22 | 1 | PE |
| 71 | 1 | 1 | 1 | 0 | 1 | 0 | 0 | 1 | 1 | 0 | 18.87 | 19 | 1 | DVT |
| 72 | 1 | 1 | 1 | 0 | 1 | 0 | 1 | 2 | 2 | 0 | 20.45 | 15 | 0 | DVT |
| 73 | 1 | 1 | 1 | 0 | 1 | 0 | 0 | 0 | 2 | 0 | 20.42 | 21 | 1 | DVT |
| 74 | 1 | 1 | 0 | 1 | 1 | 0 | 1 | 1 | 1 | 1 | 20.76 | 16 | 0 | PE |
| 75 | 0 | 0 | 1 | 0 | 1 | 0 | 1 | 0 | 1 | 0 | 21.8 | 19 | 1 | none |
| 76 | 0 | 0 | 0 | 1 | 1 | 1 | 1 | 0 | 0 | 0 | 22.955 | 42 | 0 | none |
| 77 | 0 | 0 | 0 | 1 | 1 | 0 | 1 | 1 | 0 | 0 | 22.463 | 42 | 0 | none |
| 78 | 0 | 0 | 0 | 0 | 0 | 0 | 1 | 2 | 0 | 1 | 16.9 | 29 | 1 | none |
| 79 | 0 | 0 | 0 | 0 | 0 | 0 | 1 | 1 | 0 | 1 | 18.37 | 27 | 1 | none |
| 80 | 0 | 0 | 0 | 0 | 1 | 0 | 1 | 0 | 0 | 1 | 19.53 | 20 | 0 | none |
| 81 | 0 | 0 | 0 | 0 | 0 | 0 | 0 | 0 | 1 | 1 | 20.4 | 23 | 1 | none |

In the context of the invention, a report will indicate whether the subject is heterozygous or homozygous for the effect allele, or homozygous for the non-effect allele. The report will include a probability score to develop a blood clotting disease.

For calculating the score, the risk factor determined for a single nucleotide polymorphism of the invention may be pondered by a coefficient depending on what is the contribution of said single nucleotide polymorphism in the determination of the risk in comparison with the other one single nucleotide polymorphism. Typically, the method for calculating the score is based on statistical studies performed on various cohorts of patients. The score may also include other various patient parameters (such as clinical parameters). The weight given to each parameter is based on its contribution relative to the other parameters in explaining the inter-individual variability of developing a blood clotting disease.

This probability is derived from a model that includes the risk factor determined for the rs6025 (SEQ ID NO: 3); rs1799963 (SEQ ID NO: 4); rs8176719 (SEQ ID NO: 5); rs8176750 (SEQ ID NO: 6); rs9574 (SEQ ID NO: 7); rs2289252 (SEQ ID NO: 8); rs710446 (SEQ ID NO: 9); rs4379368 (SEQ ID NO: 2); and/or rs1799853 (SEQ ID NO: 1) or any SNP in linkage disequilibrium with those SNPs cited above.

The probability score may also include clinical parameters (e.g. smoking status, the BMI, the age, the familial history of blood clotting diseases and/or the change in hormone levels) and the type of hormone used by the subject. The probability score may also be generated from a computer program for establishing such a score.

The invention claimed is:

1. A method for identifying if a woman subject undergoing a change in hormone levels is at risk of developing a blood clotting disease, the method comprising:
   determining, in a sample from said woman subject, genotyping data including the single nucleotide polymorphisms of rs1799853 (SEQ ID NO: 1) and rs4379368 (SEQ ID NO: 2), wherein the presence of allele T in rs1799853 (SEQ ID NO: 1) and allele T in rs4379368 (SEQ ID NO: 2) in heterozygous or homozygous form indicates that said woman subject has an increased risk of developing a blood clotting disease; and
   administering an effective amount of a compound adapted to the prevention of the blood clotting disease to the woman subject based on the risk for developing a blood clotting disease,
   wherein the blood clotting disease is selected from the group consisting of deep vein thrombosis, pulmonary embolism, vein thrombosis, and arterial thrombosis.

2. The method according to claim 1, wherein said method further comprises determining, in the sample, genotyping data of at least one single nucleotide polymorphism selected from the group consisting of rs6025 (SEQ ID NO: 3), rs1799963 (SEQ ID NO: 4), rs8176719 (SEQ ID NO: 5), rs8176750 (SEQ ID NO: 6), rs9574 (SEQ ID NO: 7), rs2289252 (SEQ ID NO: 8), and rs710446 (SEQ ID NO: 9).

3. The method according to claim 1, wherein said method further comprises determining, in the sample, genotyping data of the single nucleotide polymorphisms of rs6025 (SEQ ID NO: 3), rs1799963 (SEQ ID NO: 4), rs8176719 (SEQ ID NO: 5), rs8176750 (SEQ ID NO: 6), rs9574 (SEQ ID NO: 7), rs2289252 (SEQ ID NO: 8), and rs710446 (SEQ ID NO: 9).

4. The method according to claim 1, wherein said woman subject undergoing a change in hormone levels is having a contraceptive, a combined contraceptive, a hormonal replacement therapy, a progestin-only contraceptive, is pregnant, is having assisted reproductive technology, or is in postpartum period.

5. The method according to claim 1, wherein the presence or absence of at least one single nucleotide polymorphism is determined by nucleic acid sequencing and/or by PCR analysis.

6. The method according to claim 1, wherein the blood clotting disease is deep vein thrombosis or pulmonary embolism.

* * * * *